(12) United States Patent
Jordan et al.

(10) Patent No.: US 9,468,683 B2
(45) Date of Patent: Oct. 18, 2016

(54) HYBRID HYDROGELS

(71) Applicant: University of Geneva, Geneva (CH)

(72) Inventors: Olivier Jordan, Prangins (CH); Sema Gwendolyn Kaderli, Bernex (CH); Robert Gurny, Geneva (CH)

(73) Assignee: UNIVERSITY OF GENEVA, Geneva (CH)

( * ) Notice: Subject to any disclaimer, the term of this patent is extended or adjusted under 35 U.S.C. 154(b) by 0 days.

(21) Appl. No.: 14/424,907

(22) PCT Filed: Aug. 21, 2013

(86) PCT No.: PCT/EP2013/002523
§ 371 (c)(1),
(2) Date: Feb. 27, 2015

(87) PCT Pub. No.: WO2014/032780
PCT Pub. Date: Mar. 6, 2014

(65) Prior Publication Data
US 2015/0202295 A1    Jul. 23, 2015

Related U.S. Application Data

(60) Provisional application No. 61/693,803, filed on Aug. 28, 2012.

(51) Int. Cl.
| | |
|---|---|
| *A01N 25/00* | (2006.01) |
| *A61K 47/00* | (2006.01) |
| *A61K 47/02* | (2006.01) |
| *A61K 47/26* | (2006.01) |
| *A61K 9/06* | (2006.01) |
| *A61K 47/36* | (2006.01) |
| *A61K 31/192* | (2006.01) |

(52) U.S. Cl.
CPC ............... *A61K 47/02* (2013.01); *A61K 9/06* (2013.01); *A61K 31/192* (2013.01); *A61K 47/26* (2013.01); *A61K 47/36* (2013.01)

(58) Field of Classification Search
None
See application file for complete search history.

(56) References Cited

FOREIGN PATENT DOCUMENTS

| CN | 102600019 | 7/2012 |
| WO | WO-02/30990 A1 | 4/2002 |
| WO | WO-2004/011503 A1 | 2/2004 |
| WO | WO-2005113608 A1 | 12/2005 |

OTHER PUBLICATIONS

"Characterization." Merriam-Webster.com. Merriam-Webster, n.d. Web. Apr. 15, 2016.*
International Search Report of PCT/EP2013/002523 dated Oct. 22, 2013.
Guo, Gang et al; "Medical hydrogel dressing for use during acute and chronic wound healing process in clinic, has hydrogel layer whose side part is fixed on medical adhesive tape, where hydrogel layer is made of sodium alginate"; AN 2012-N57604 XP002715125; Thomson Scientific, London GB; Jul. 25, 2012.

* cited by examiner

*Primary Examiner* — Jeffrey H Murray
(74) *Attorney, Agent, or Firm* — Wolf, Greenfield & Sacks, P.C.

(57) ABSTRACT

The present invention relates to compositions and pharmaceutical compositions having a hyaluronic acid; a chitosan; and at least one ionic compound in hydrogel form, their use in medical applications and methods of making same as well as medical devices comprising same.

45 Claims, 5 Drawing Sheets

HYBRID HYDROGELS

CROSS-REFERENCE TO RELATED APPLICATIONS

This application is the national phase under 35 U.S.C. §371 of PCT International Application No. PCT/EP2013/002523, filed Aug. 21, 2013, which claims the benefit of U.S. Provisional Patent Application No. 61/693,803, filed Aug. 28, 2012, the entire contents of the aforementioned applications are hereby incorporated herein by reference.

The present invention relates to compositions and pharmaceutical compositions forming hydrogels, their use in medical applications and methods of making same as well as medical devices comprising same.

BACKGROUND OF THE INVENTION

Hyaluronic acid (HA) and compositions comprising HA are known for long time. HA has been combined with various other compounds and applied in a number of medical applications. In gel formulations, such applications include treatment of joint problems, and particularly for knee joint problems.

An approved medical treatment is e.g. Synvisc-One™ (hylan G-F 20) of Genzyme Corporation indicated for the treatment of pain in osteoarthritis (OA) of the knee in patients.

Various compositions containing HA with other components are known in the art. Chitosan is of particular interest for its combination of biocompatibility, biodegradability, bioadhesivity as well as for its wound healing-promoting and bacteriostatic properties. (Pangburn S H, Trescony P V, Heller J. Lysozyme degradation of partially deacetylated chitin, its films and hydrogels. Biomaterials; 1982; 3:105-108; Tomihata K, Ikada Y. In vitro and in vivo degradation of films of chitin and its deacetylated derivatives. Biomaterials 1997; 18:567-575; Lehr C M, Bouwstra J A, Schacht E H, Junginger H E. In vitro evaluation of mucoadhesive properties of chitosan and some other natural polymers. Int J Pharm 1992; 78:43-48; Ueno H, Mori T, Fujinaga T. Topical formulations and wound healing applications of chitosan. Adv Drug Deliv Rev 2001; 52:105-115; Liu N, Chen X G, Park H J, Liu C G, Liu C S, Meng X H, Yu L J. Effect of MW and concentration of chitosan on antibacterial activity of *Escherichia coli*. Carbohydr Polym 2006; 64:60-65.)

Combining HA and chitosan has been attempted in many ways. For example, U.S.2009/0238874 A1 describes Biomimetic compositions reinforced by a polyelectrolytic complex of hyaluronic acid and chitosan. HA and chitosan are assembled in dry form without any excipient addition. The compounds are arranged as polyionic complexes representing a network of insoluble fibers and thin membranes wherein a phase separation leads to segregated HA-rich and chitosan-rich domains. Such a distribution is however undesirable for many applications.

A publication of Denuziere, A. et al. (Biomaterials 19: 1275-1285, 1998), describes chitosan-chondroitin sulfate and chitosan-hyaluronate polyelectrolyte complexes.

U.S.2006/0166928 A1 having the title "hyaluronic acid derivative gel and method for preparing the same" describes derivatized HA covalently linked to chitosan via EDC/NHS amidation having a HA:chitosan ratio of 5 to 40. The compound shows thermogelling ability.

U.S. 2009/0238875 titled "Chitosan or hyaluronic-poly (ethylene oxide) and chitosan-hyaluronic acid-poly (ethylene oxide) based hydrogels and manufacturing method therefore" refers to chitosan-polyethyleneoxide (PEO), HA-PEO, chitosan-HA-PEO hydrogels obtained by chemical addition via acrylate chemistry for use in delivering proteins and peptides.

CN 10167600 is concerned with HA-chitosan biomembranes.

U.S. Pat. No. 7,524,514 relates to biomimetic compositions reinforced by a polyelectrolytic complex of HA and chitosan.

Hydrogels consist of three-dimensional networks of natural or synthetic polymers dispersed in water. Physical or chemical crosslinking ensure the insolubility and stability of the polymer gel. Hydrogels exhibit high absorbance for water and can contain as much as 99.9% water. It can be desired to have hydrogels which are clear and do not contain any aggregates. Hydrogels formed from HA and chitosan without a significant amount of aggregates have so far not been described and would be useful for a number of medical applications.

The above state of the art does neither disclose nor suggest the below described invention. In particular, the prior art does not disclose or suggest transparent aggregate-free gels.

SUMMARY OF THE INVENTION

In one aspect the invention relates to a composition comprising or consisting of i. a hyaluronic acid; ii. a chitosan; and iii. at least one ionic compound, characterized in that the composition is a hydrogel and wherein the hydrogel exhibits high homogeneity, preferably characterized by non-occurrence of aggregates, more preferably by non-occurrence of visible aggregates, as preferably seen under visual inspection or more preferably by visible microscopic analysis. Preferably the analysis of aggregates can be performed using absorbance and/or turbidity measurement.

In another aspect the invention concerns a pharmaceutical composition comprising in addition one or more pharmaceutically active compounds.

In yet another aspect the invention relates to a method of making a composition or pharmaceutical composition comprising the steps of i. providing a solution comprising chitosan; ii. adding at least one ionic compound, iii. adding hyaluronic acid as a powder; iv. mixing the components; and v. preferably letting the thus mixed composition rest for about 12 hours, preferably about 14 hours and most preferably about 16 hours, at 4° C.

In yet another aspect the invention relates to a composition as described above for use in a medical application.

In yet another aspect the invention relates to a composition as described above for use as a delivery means or/and as a medical device.

DETAILED DESCRIPTION OF THE INVENTION

The prior art describes hyaluronic acid (HA) compositions and the combination of HA with other compounds like chitosan. Also hydrogels are described in the state of the art as well as various non-medical and medical uses of such compositions.

The respective prior art compositions and hydrogels exhibit specific characteristics depending on the particular composition. The characteristics of the respective compositions are not always advantageous for all possible applications.

Accordingly it is an object of the present invention to provide HA-chitosan compositions useful as hydrogels having advantageous characteristics, or at least to improve the state of the art of HA-chitosan hydrogels.

This object is solved by a composition according to the invention comprising or consisting of i. a hyaluronic acid; ii. a chitosan; and iii. at least one ionic compound, characterized in that the composition is a hydrogel and wherein the hydrogel exhibits high homogeneity, preferably characterized by non-occurrence of aggregates, more preferably by non-occurrence of visible aggregates, as preferably seen under visual inspection or more preferably by visible microscopic analysis.

The inventors have surprisingly found that the addition of an excipient, known as any constituent of a medicinal product that is not an active substance (adjuvants, stabilizers, antimicrobial preservatives, diluents, antioxidants) according to the European Pharmacopeia, leads to advantageous hydrogels with reduced aggregation and in a preferred embodiment do not contain any visible aggregates. The hydrogel obtained by the invention is optically clear.

The simple mixing of chitosan and HA in a hydrated or dry form as described in the prior art will disadvantageously result in heterogeneous gels. The two biopolymers form polyelectrolyte complexes at the region of intimate physical contact resulting in a network of insoluble fibers and thin membranes leading to segregated HA-rich and chitosan-rich gel domains with non-homogenous properties.

The invention solves this problem and provides for hydrogel compositions which are homogenous, stable and biocompatible comprising HA and chitosan in chosen ratios.

It was surprising that the addition of an excipient, and preferably specific salts or combination of salts, could lead to such advantageous compositions and hydrogels.

Another advantage being that such hydrogels exhibit superior characteristics as compared to the known hydrogels or HA/chitosan compositions. These improved features are in particular in medical applications of great benefit because e.g. the frequency of injections may be reduced. In the context of e.g. injection in the articulation an extended hyaluronic acid retention time may be achieved.

Another advantage is that in contrast to known HA/chitosan compositions no covalent modification of the basic components is required to achieve homogeneous hydrogels. Accordingly, unpredictable compound features and possible side effects due to the chemical modification can be avoided. This will not only have a benefit for the treated patients but will improve safety and biocompatibility. Moreover, it will facilitate regulatory approval and will thus be more cost efficient for industry and for the health system.

The invention has thus solved the problem of heterogeneous mixtures of HA/chitosan and provides homogenous hydrogels.

In sum, the invention provides advantageously for a hydrogel with two known and well characterized components with improved material features and improved secondary effects like cost saving.

The results achieved with the invention are also astonishing because the inventors decided to embark on an approach generally considered not prone to success. Moreover, the inventors combined two compounds, i.e. HA and chitosan, which according to the general point of view in chemistry should not be combined in this manner. In fact the general opinion was not to mix HA and chitosan because the compounds were considered incompatible. Nevertheless the inventors decided so against the chemical paradigm.

Surprisingly, the inventors were able to obtain transparent gels, apparently devoid of particles, fibers or other aggregates usually found in mixtures of oppositely charged electrolytes. The ability to have only one homogeneous phase in the composition should ensure a tighter control of the properties of the formulation, thus ensuring an easier regulatory pathway as well as a better market acceptability. In addition, this result could be obtained without any increase of viscosity compared to that of the separate components/constituents.

The composition of the invention can use any suitable hyaluronic acid and the skilled person will adapt the amount contained in the composition according to the final applications and its needs. In a preferred embodiment the composition comprises hyaluronic acid as sodium hyaluronate, preferably obtained from a Streptococcal bacterial source.

Any suitable molecular mass distribution will be chosen depending on the composition components and the possible use. In a preferred embodiment the composition is characterized by a molecular mass distribution of from about 2 to 3000 KDa, more preferably about 1300 KDa.

The skilled person will chose for the composition a suitable polydispersity index, defined as the ratio of the mass-averaged molar mass Mw over the number-averaged molar mass Mn, Preferably the sodium hyaluronate (D-glucuronic acid/GlcA) is characterized by a polydispersity index of about 1 to 1.6, more preferably from 1.07 to 1.55, even more preferably it is about 1.2.

The chitosan used in the composition according to the invention can be any available chitosan which can be purchased from known chemical suppliers. The chitosan can be chemically modified or unmodified in any suitable manner. In a preferred embodiment the chitosan is a modified or unmodified poly-$\beta_{1-4}$-glucosamine (chitosan) obtained from *Agaricus bisporus*, more preferably characterized by a deacetylation degree of about 45 to about 70%, even more preferably from about 50 to about 60%, even more preferably of about 50% DDA (NMR).

The molecular mass distribution will also be adapted according to the design of the composition and possible uses as appropriate. Preferably, the chitosan has a molecular mass distribution of about 1 to 2000 KDa, more preferably about 50 to 150 KDa, even more preferably about 50 to 100 KDa or about 110 to 130 KDa, even more preferably of about 120 KDa, even more preferably about 100 KDa.

The polydispersity index can vary but a polydispersity index of 1.6 or less is preferred, more preferred is one of 1.4 or less, even more preferred is one of 1.1 or less.

The pH may influence the compounds characteristics and will be chosen to be in an advantageous range. Preferably the composition exhibits a pH of about 6 to 8, more preferably about 6.5 to 7.5. The pH reached by the formulations are compatible with the physiology of many therapeutic application routes.

The inclusion of ionic compounds may be advantageous and thus the composition in a preferred embodiment contains an ionic compound, preferably the ionic compound comprises $Ca^{2+}$, $Na^+$, $Mg^{2+}$ or/and $Al^{3+}$ ions.

In the composition according to the invention the ratios of the components i.), ii.) and iii.) can vary and will be chosen in a way to optimize the characteristics of the composition. In a preferred embodiment the compounds i.) and ii.) are present in the composition in a weight ratio of 1000:1 to 1:2, more preferably 40:1 to 3:2.

In certain applications the amount of chitosan may be kept at a lower range in order to avoid medical side effects connected with this compound or carried over impurities from the production process, while in other applications the content of chitosan will be particularly high. Same applies to HA in the composition of the invention.

It will be also useful in certain embodiments and depending on the particular use to include preferably a buffer in the composition. The skilled person will chose the buffer best suitable in the context of the use of the composition. Preferably the buffer is a boric acid/sodium tetraborate buffer or a phosphate buffer. Such a composition may have a pH advantageous in the context of the application of the composition and preferably the composition has a pH of from about 5.5 to 7.5, more preferably from about 6 to 7, and even more preferably about 7.

A particularly preferred embodiment contains NaCl, preferably with other buffer components.

The osmolarity will be an important aspect in certain uses and it will thus be adapted and optimized depending thereupon. In a preferred embodiment the composition is formulated as an isotonic or slightly hypertonic solution, preferably having an osmolarity ranging from 280 to 500 mOsmoles.

In medical applications purity and a low degree of immunogenicity is an important point in the context of safety considerations of a medical product and has an impact on regulatory issues. It is not always foreseeable and cannot be always predetermined what impurities will be carried over from a certain production process. Moreover, it is not with certainty predictable what molecules of impurities will cause an unwanted immunogenic effect. In the context of the invention it is advantageous to reduce residual protein content originating from the production of the single components of the compound of the invention. It will thus be advantageous if the content of the residual protein is limited to a certain amount in order to prevent unwanted immunological side effects and to increase safety of the compound. Accordingly, in a preferred embodiment the content of residual protein is less than 0.5%, preferably less than 0.2%, more preferably less than 0.1%.

Viscosity of the compound is a major aspect of the composition of the invention and thus the compound components will be mixed in a ratio to arrive at a suitable viscosity for the wanted use or method of use.

The skilled person will appreciate that e.g. for a topical application a high viscosity is needed whereas an application in ophthalmology or for dermal injection will require a lower viscosity and intra-articular administration will require a medium viscosity.

In preferred embodiments the viscosity can be adapted by choosing the single components in a specific manner wherein the composition is characterized by a viscosity of 0.05-10 Pa·s, preferably 0.5 to 5 Pa·s, more preferably 5 Pa·s as measured by rotational rheometry with a 35 mm diameter/ 2° cone-plate geometry at a 46 $s^{-1}$ shear rate. For intra-articular application a wide range of typical viscosities ranging from 0.05 to 50 Pa·s are used. Similar viscosities may be used for ophthalmic applications. Topical application can also be performed with highly viscous—several $10^2$ Pa·s—or viscoelastic formulations. Any chitosan obtainable on the market or by chemical modification can be applied in the invention. It may be advantageous for human and medical uses to use preferably chitosan obtained from a non-animal origin, preferably a fermentation process or extraction from fungi. Non-animal source of polymer advantageously provides a reduced risk of immunological reaction.

The composition according to the invention can be any composition in any purity grade depending on the uses it is applied in. The grade and standard of purity will depend on the technical, legal or regulatory provisions and may vary from country to country. The skilled person will understand which starting materials to use to arrive at certain standards and purity grades.

In another aspect the invention relates to a pharmaceutical composition.

In another aspect the composition or pharmaceutical composition according to the invention forms hybrid hydrogels. Hybrid refers to the nature of an entity formed or composed of heterogeneous element, more specifically to a hydrogel based on the association of two distinct polymers, as opposed to classical one-component hydrogels (Matricardi P et al., Macromolecular Research 19 (12): 1264-1271, 2011; Epstein-Barach H et al, Acta Biomaterialia 8: 1703-1709, 2012; Zhang L. et al, Carbohydrate Polymers 84:118-125, 2011)

In the literature "hybrid hydrogels" covers the association of two very different components into a gel-like structure: nanoparticles in a gel, inorganic aggregates in a gel, or the association of a synthetic polymer with peptide or proteins. In a preferred embodiment of the invention the term "hybrid" is used in a more specific way, i.e. two different hydrophilic polymers in a gel are combined. In this preferred embodiment, hydrogels can be distinguished into more preferably mono-component hydrogel and even more preferably hybrid hydrogels.

The hydrogel of the invention is preferably transparent.

A liquid is considered transparent or clear if its clarity is the same as that of water measured according to European Pharmacopeia standard method at daylight viewing vertically against a black background. The perfect transparency of the formulation gives the advantage of an increased reproducibility of preparation as well as a better controlled use.

A particular advantage of a preferred embodiment is that the hydrogel formed by the composition of the invention maintains transparency or/and its pH after an autoclaving/ steam sterilization cycle, preferably wherein this cycle is characterized by a temperature of 121 ° C. and a duration of preferably 10 min.

Surprisingly, the addition of chitosan to the HA formulation increases the HA resistance to autoclaving as shown by the reduction of autoclaving-induced viscosity loss. This protective effect of the chitosan-HA combination with respect to thermal degradation is expected to facilitate the terminal sterilization of the final hybrid gel product, and thus facilitate the preparation of sterile therapeutic formulations.

It is preferred that the composition or pharmaceutical composition of the invention is essentially free from aggregates of hyaluronic acid and chitosan.

It is particularly preferred that the composition or pharmaceutical composition contains less than 10%, preferably less than 5%, more preferably less than 1% and most preferably less than 0.01% visible aggregates as seen by light microscopy under low magnification (10×).

In another preferred embodiment of the invention the hyaluronic acid is stabilized to prevent aggregation with other formulation components.

The composition or pharmaceutical composition can be combined with other compounds or mixtures of compounds as long as they do not interfere with the major composition compounds and preferably as long as they do not interfere with the advantageous characteristics of the invention.

The presence of chitosan in the novel hybrid gel opens the way to the incorporation of anionic drugs, that may bind to the chitosan cationic groups and be released slowly upon ionic exchange with physiological ions, thus resulting in an extended release or improved drug incorporation compared to a HA gel. Such features may be of high therapeutic value. Similarly, hydrophobic chitosan-drug interaction may allow the incorporation of drugs usually not loadable into classical mono-component HA gels.

Thus, in a preferred embodiment the composition or pharmaceutical composition comprises in addition one or more pharmaceutically active compounds. The pharmaceutical active compound may be any active compound compatible with the composition of the invention and preferably comprises an active compound selected from the group consisting of drugs, cytotoxic agents, proteins, hormones, nucleic acids, vectors, cells or/and lipids.

In particular the active compound is selected from anti-oxidant drugs, anti-inflammatory drugs, preferably a non-steroidal anti-inflammatory drug such as ibuprofen, drugs for ophthalmology, molecules promoting cell adhesion, differentiation or growth.

The viscosity of the hydrogel can be tailored to the particular use and the adaptation of the viscosity will be achieved by way of mixing the components of the composition of the invention in ratios which will lead to the desired viscosity. In preferred embodiments the composition or pharmaceutical composition has a viscosity of 0.05-10 Pa·s, preferably 0.5 to 5 Pa·s, more preferably 5 Pa·s as measured by rotational rheometry with a 35 mm diameter/2° cone-plate geometry at a 46 s$^{-1}$ shear rate.

The composition of the invention can be manufactured by way of a method of making a composition or pharmaceutical composition comprising the steps:
 i. providing a solution comprising chitosan;
 ii. adding ionic compounds as powders
 iii. preferably adding hyaluronic acid as a powder;
 iv. mixing the components; and
 v. preferably letting the thus mixed composition rest overnight at 4° C.

The manufacturing method, more specifically the order of components addition, permits the preparation of a non-aggregated and homogeneous formulation. It is important to add the stabilizing additive to one of the polymers before mixing, since aggregation is difficult to reverse. Adding HA as a powder is a preferred process to ensure enhanced homogeneity of the final composition; it is however possible to add HA as a viscous solution.

"Homogeneous gel" is understood here as a particular aspect of transparency, not related to the presence of particulates but to the absence of fluctuations of refractive index, which would distort the image when looking through the cuvette containing the gel. A complete mixing of the two polymers can be characterized by optical homogeneity, in contrast incomplete mixing will induce refractive index fluctuations.

The components applied in this method of making have been described above and will be more apparent from the Example section. This applies in particular to the origin of the compounds applied in the method of making and their purity grade and their origin or the methods and sources the single compounds are obtained from.

In a preferred embodiment of the method the chitosan is used as a stock solution comprising or consisting of 2.5% (m/v) of chitosan in hydrochloric acid 0.1 M, pH 6.5.

The compositions thus obtained or with other methods can be used in a medical application.

The medical indication is not limited to any particular disease or disorder, preferably the composition of the invention is used for the application in the use of an ophthalmic, topical, systemic or intra-articular application.

Other medical uses, methods of treating and indications can relate to regeneration of body tissues, the gel eventually incorporating drugs to promote healing at specific tissue sites. The way and route of application is generally not restricted and the composition can be applied in any known route of application, in particular it is suitable for a topical, i.v., i.m., s.c. application, application into a joint or into an eye.

The composition and hydrogel of the invention can also be used as a delivery means or/and as a medical device.

In another aspect the invention is directed to a composition or pharmaceutical composition as described above for use in aesthetic applications, preferably for cosmetic applications.

The composition may be used with suitable adjuvants or in combination with other active compounds as frequently applied in cosmetic application and which are well known to the skilled person. In a preferred embodiment the composition is applied intradermally or subdermally.

The positive characteristics of the hydrogel of the invention are particularly useful in the aesthetic applications and for cosmetic purposes. The invention can thus be applies e.g. in all cosmetic areas wherein a tissue appearance shall be improved or the volume be increased at defined areas, e.g. the lips, other facial parties.

Another area of application is e.g. the treatment of wrinkles. The side effects are few compared to the number of patients treated. The inventive compositions give security and efficiency to the patient, which is important for cosmetic indications.

The skilled person in the field of cosmetic surgery and aesthetic treatments is well aware of hyaluronic acid treatments in his field. Equally well and with improved results the skilled person will appreciate that the inventive components will be applicable here and provide advantageous treatment results.

The injections can be performed as one injection or as series of repeated injections. Also the dosage and volume injected will vary depending on the particular circumstances.

The above described preferred features of the invention can be found in the invention as single features or one or more of these features can be combined in the invention. Accordingly, it is within the reach of the invention to produce or use any combination of features which have been disclosed throughout the specification or in the examples and claims. The skilled person will appreciate that particular combinations of preferred features will have advantageous effects which can be proven by experimentation obvious to the skilled person in the field of the invention.

EXAMPLES

Example 1

Fabrication of a Chitosan Stock Solution

A chitosan (Cs) stock gel is prepared as follows: a 2.5% Cs solution in hydrochloric acid 0.1M is brought to pH 6.5 by dropwise addition of sodium hydroxide 1M. Gel is diluted to 2% and left at rest for one night at 4° C.

Example 2

Fabrication of Hybrid Hydrogel (Preferred Formulation 1)

Weighed quantities of excipients (NaCl, $Na_2HPO_4$, $NaH_2PO_4$) are dissolved in water to obtain the desired concentration. Chitosan is added and the composition is stirred, e.g. with a magnetic stirrer, at room temperature until complete dissolution of the polysaccharide (typically overnight). HA powder is then added and the suspension left at rest at 4° C. for one night. Mixing with the paddle mixer at 300 rotations/minute for 10 minutes and rest at 4° C. overnight will lead to the formation of a homogenous hybrid gel.

Example 3

Fabrication of a Hybrid Hydrogel (Preferred Formulation 2)

Weighed quantities of excipients ($CaCl_2$, boric acid, sodium tetraborate) are dissolved in water to obtain the desired concentration. Chitosan is added and the composition is stirred, e.g. with a magnetic stirrer, at room temperature until complete dissolution of the polysaccharide (typically overnight). HA powder is then added and the suspension left at rest at 4° C. overnight. Mixing with the paddle mixer at 300 rotations/minute for 10 minutes and rest at 4° C. overnight will lead to the formation of a homogenous hybrid gel.

Example 4

Steam Sterilization (Autoclaving) of Hybrid Gels Formulation

Figure 4:
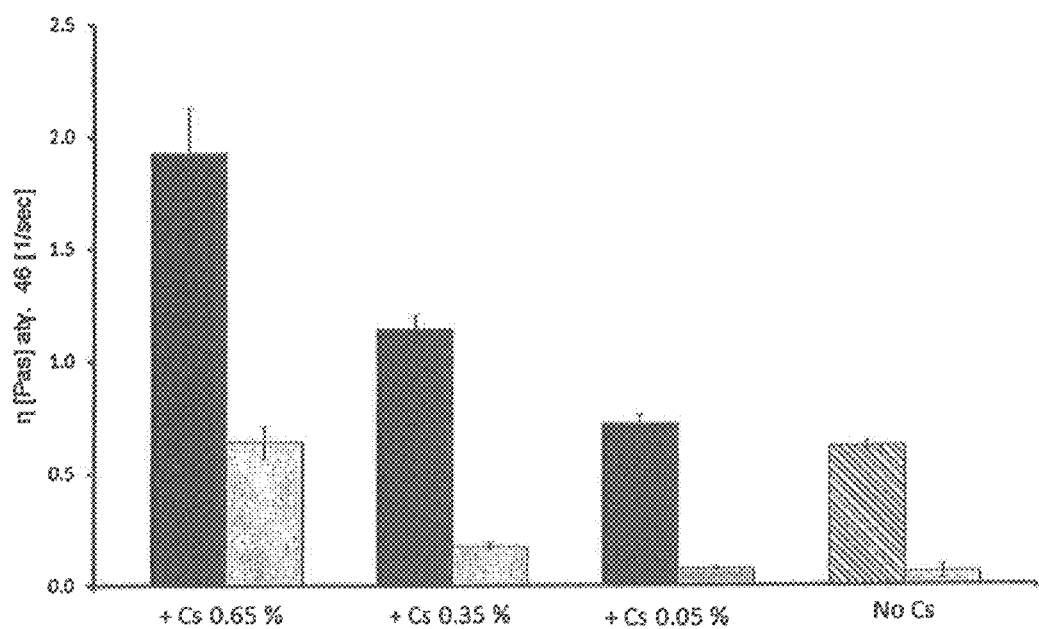
FIG. 4: Viscosities of hybrid hydrogel formulations with 1% $CaCl_2$ at 0.65, 0.35 and 0.05% of chitosan (Cs) in comparison with HA 1% formulation measured at a shear rate (γ.) of 46 [1/sec]. Left bars represent the viscosity before autoclaving, right bars the viscosity after 15 minutes of autoclaving.
Figure 5:
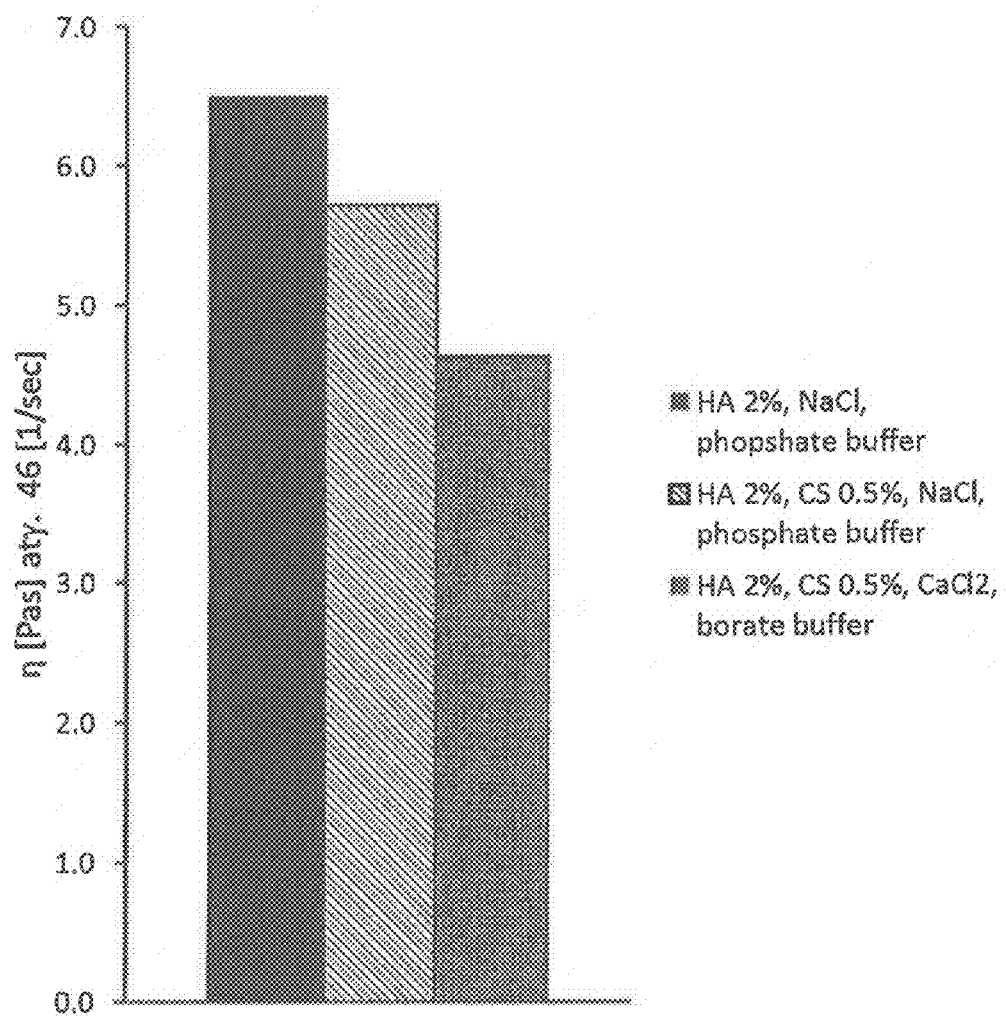
FIG. 5: Viscosities of autoclaved hybrid hydrogel formulations with 2% HA and 0.5% chitosan (Cs) in comparison with HA 2% autoclaved formulation (at γ·46 [1/sec]) after 10 min autoclaving.

Two milliliters of the formulation are poured in a 5 ml penicillin glass, closed with a rubber cork and sealed. Autoclaving is performed for 10 minutes at 121° C., vapor is forced to go out and the autoclave opened before complete cooling so as to reduce the total time of the cycle to 30 minutes. FIG. 4 illustrates the decrease of formulation viscosity under autoclaving, showing that viscosity decreases by 10-fold for the HA without chitosan, whereas it decreases by only 3-fold for the hybrid gel incorporating 0.65% of Cs.

Example 5

Drug Loading Into a Hybrid Gel Formulation 1

Ibuprofen 0.5% w/w is added together with weighed excipients (NaCl, $Na_2HPO_4$, $NaH_2PO_4$) to water in adequate quantity to reach the desired concentration. Chitosan is added and the composition is stirred, e.g. with a magnetic stirrer, at room temperature until complete dissolution (typically overnight). HA powder is then added and the suspension left at rest at 4° C. overnight. Mixing with the paddle mixer at 300 rotations/minute for 10 minutes and rest at 4° C. overnight will lead to the formation of a homogenous hybrid gel.

Example 6

Characterization of Absence of Aggregation and Homogeneity

The hydrogels obtained from example 2 were inspected visually according to European Pharmacopeia standard method at daylight viewing vertically against a black background.

Figure 1:
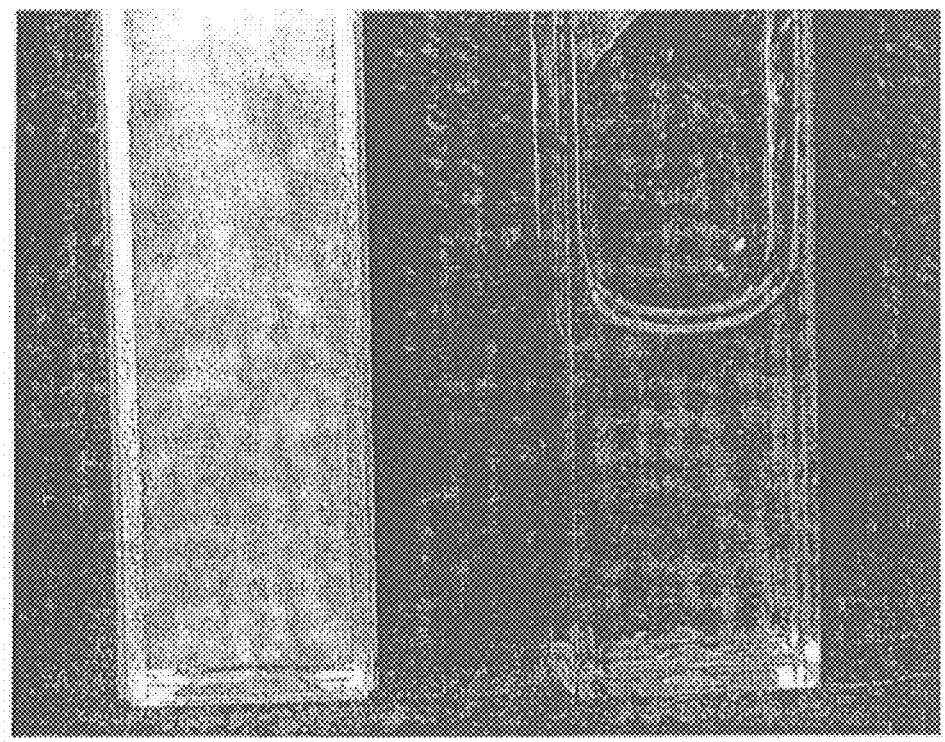
FIG. 1: Picture of an aggregated formulation, obtained from simple chitosan and HA mixing (Left), compared to a non-aggregated formulation obtained upon addition of appropriate excipients of example 2 (right). Both formulations are placed in spectrophotometric disposable cuvettes.
Figure 2:
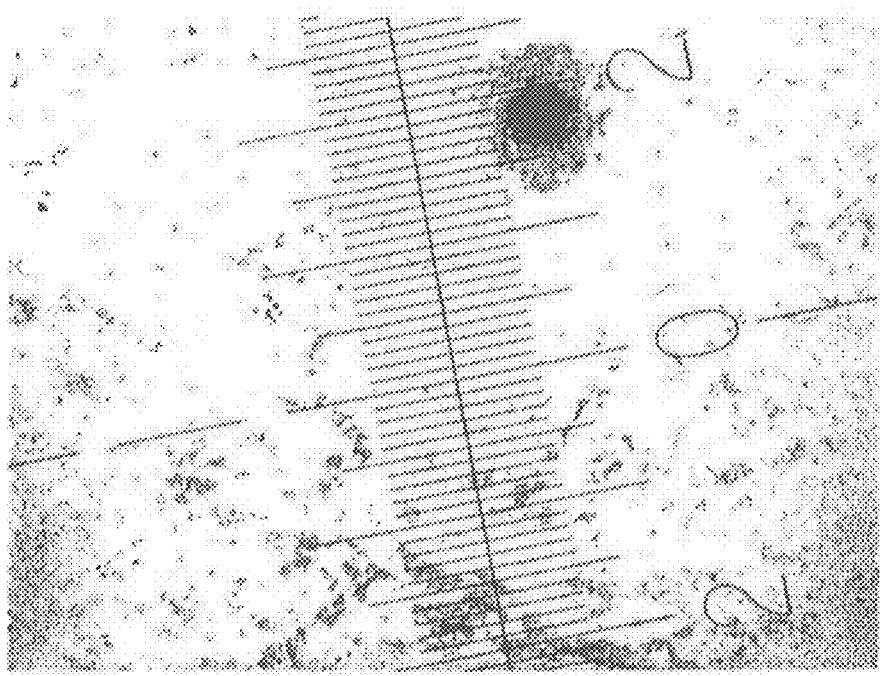
FIG. 2/3: Picture of an aggregated formulation (FIG. 2) and a non-aggregated formulation (FIG. 3) under phase contrast microscopy (10× magnification, pH1 objective).

FIG. 1 illustrates the result of the test. Against a black background, formulation on the left side is clearly turbid showing presence of aggregates. The formulation on the right side is transparent. Further inspection using phase contrast optical microscopy at low magnification (10× objective) shows the presence of eventual aggregates (FIG. 2).

Figure 3:
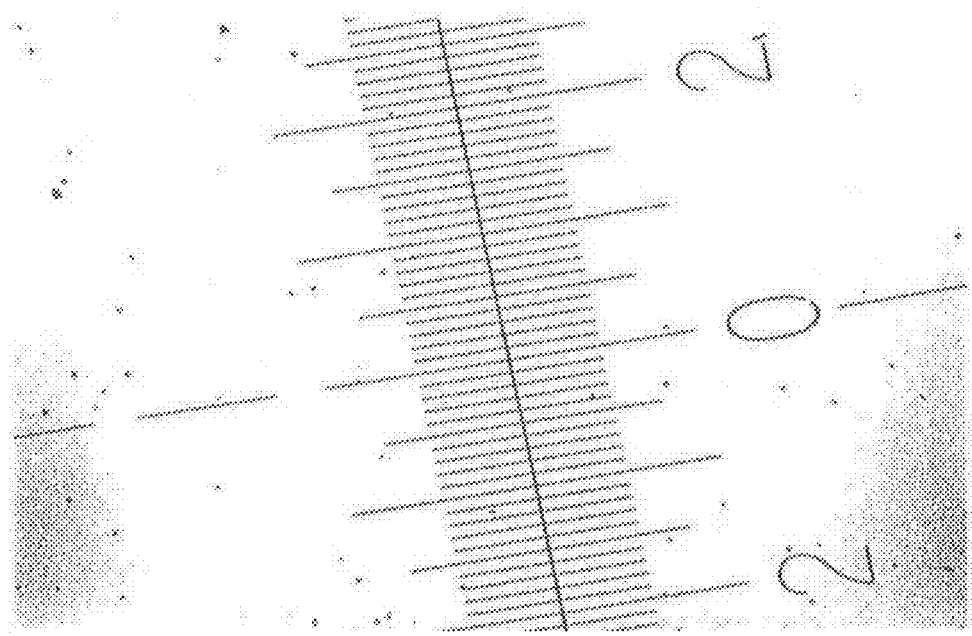

When looking through the cuvette shown on right side of FIG. 1, an unaltered, undistorted image is seen, indicating the absence of major fluctuations in refraction, and thus homogeneity of the gel. Optical microscopy confirms the absence of aggregates (FIG. 3).

Example 7

Viscosity Measurement

The viscosity is measured with a Haake Rheostress 1 (Haake, Karlruhe, Germany) using a titanium cone and plate geometry (diameter 35)mm/2°). Temperature was maintained at 37° C. with a thermostatic bath. For the rotational mode, shear rate varied from 0.1 $s^{-1}$ to 100 $s^{-1}$, the viscosity value at 46 $s^{-1}$ was retained as a characteristic of the formulation. For the oscillation mode, under constant stress, shear rate varied from 0.1 to 100 Pa at 1 Hz at 37° C. Using the formulation of example 3, FIG. 4 shows that final viscosity can be tailored by adjusting chitosan concentration.

The invention claimed is:

1. Composition comprising or consisting of
   i. a hyaluronic acid;
   ii. a chitosan; and
   iii. at least one ionic compound,
   characterized in that
   the composition is a hydrogel and wherein the hydrogel exhibits high homogeneity, characterized by non-occurrence of aggregates.

2. Composition according to claim 1 wherein the hyaluronic acid is a sodium hyaluronate.

3. Composition according to claim 2 wherein the sodium hyaluronate (D-glucuronic acid/GlcA) is characterized by a polydispersity index of about 1 to 1.6.

4. Composition according to claim 1 wherein the chitosan is a modified or unmodified poly-$B_{1\_4}$-glucosamine (chitosan) obtained from *Agaricus bisporus*.

5. Composition according to claim 1 wherein the ionic compound comprises $Ca^{2+}$, $Na^r$, $Mg^{2+}$ or/and $Al^{3+}$ ions.

6. Composition according to claim 1 wherein the compounds i.) and ii.) are present in the composition in a weight ratio of 1000:1 to 1:2.

7. Composition according to claim 1 which in addition comprises a buffer.

8. Composition according to claim 7 wherein the buffer is a boric acid/sodium tetraborate buffer or a phosphate buffer.

9. Composition according to claim 7 wherein the composition has a pH of from about 5.5 to 8.0.

10. Composition according to claim 1 which is formulated as an isotonic or slightly hypertonic solution or/and having an osmolarity ranging from 280 to 500 mOsmoles.

11. Composition according to claim 1 characterized by a viscosity of 0.05-10 Pa·s as measured by rotational rheometry with a 35 mm diameter/2° cone-plate geometry at a 46 $s^{-1}$ shear rate.

12. Composition according to claim 1 wherein chitosan is obtained from a non-animal origin, preferably a fermentation process or extraction from fungi.

13. Composition according to claim 1 wherein the composition is a pharmaceutical composition.

14. Composition according to claim 1 wherein the composition or pharmaceutical composition is a hybrid hydrogel.

15. Composition according to claim 1 wherein the composition or pharmaceutical composition is essentially a transparent hydrogel.

16. Composition according to claim 1 wherein the composition maintains transparency or/and its pH after an autoclaving/steam sterilization cycle.

17. Composition according to claim 1 wherein comprising in addition one or more pharmaceutically active compounds.

18. Method of making a composition or pharmaceutical composition according to claim 1 comprising the steps:
   i. providing a solution comprising chitosan;
   ii. adding at least one ionic compound as powder
   iii. preferably adding hyaluronic acid as a powder;
   iv. mixing the components; and
   v. preferably letting the thus mixed composition rest overnight at 4° C.

19. Method according to claim 18 wherein the chitosan is characterized as defined in any of the preceding claims.

20. Method according to claim 18 wherein the hyaluronic acid is characterized as defined in any of the preceding claims.

21. Method according to claim 18 wherein the chitosan is used as a stock solution comprising or consisting of 2.5% (m/v) of chitosan in hydrochloric acid 0.1 M, pH 6.5.

22. A method of treating joint pathologies, articular diseases, eye pathologies, skin treatment, tissue regeneration applying a composition according to claim 1 to a subject in need thereof.

23. The composition of claim 1, wherein the hydrogel exhibits non-occurrence of visible aggregates.

24. The composition of claim 1, wherein the hydrogel exhibits non-occurrence of visible aggregates, as measurable by absorbance and turbidity measurement.

25. The composition of claim 1, wherein the hydrogel exhibits non-occurrence of visible aggregates, as measurable by visible microscopic analysis.

26. The composition according to claim 1 wherein the hyaluronic acid is a sodium hyaluronate obtained from a Streptococcal bacteria.

27. The composition according to claim 1 wherein the hyaluronic acid is a sodium hyaluronate obtained from a Streptococcal bacteria, and has a molecular mass distribution of from about 2 to 3000 KDa.

28. The composition according to claim 2 wherein the sodium hyaluronate (D-glucuronic acid/GlcA) has a polydispersity index of about 1.07 to 1.55.

29. The composition according to claim 2 wherein the sodium hyaluronate (D-glucuronic acid/GlcA) has a polydispersity index of about 1.2.

30. The composition according to claim 4, has a deacetylation degree of about 45 to about 70%.

31. The composition according to claim 4, has a deacetylation degree from about 50 to about 60%.

32. The composition according to claim 4, has a deacetylation degree of about 50% DDA (NMR).

33. The composition according to claim 4, wherein the chitosan has a molecular mass distribution of about 1 to 2000 KDa.

34. The composition according to claim 4, wherein the chitosan has a molecular mass distribution of about 100 to 150 KDa.

35. The composition according to claim 4, wherein the chitosan has a molecular mass distribution of about 50 to 100 KDa.

36. The composition according to claim 4, wherein the chitosan has a molecular mass distribution of about 110 to 130 KDa.

37. The composition according to claim 4, wherein the chitosan has a molecular mass distribution of about 120 KDa.

38. The composition according to claim 4, wherein the chitosan has a molecular mass distribution of about 100 KDa.

39. The composition according to claim 4, having a polydispersity index of 1.1 or more.

40. The composition according to claim 4, having a polydispersity index of 1.4 or more.

41. The composition according to claim 4, having a polydispersity index of 1.6 or more.

42. The composition according to claim 1 wherein the compounds i.) and ii.) are present in the composition in a weight ratio of 3:2 to 40:1.

43. The composition according to claim 11 having a viscosity of 0.5 to 5 Pa·s.

44. The composition according to claim 11 having a viscosity of 5 Pa·s.

45. The composition according to claim 1 wherein the composition maintains transparency or/and its pH after an autoclaving /steam sterilization cycle, wherein this cycle is carried out at a temperature of 121° C. and a duration of 10 minutes.

* * * * *